(12) United States Patent
Sandberg et al.

(10) Patent No.: US 7,295,585 B2
(45) Date of Patent: Nov. 13, 2007

(54) METHOD FOR NOISE CANCELLATION BY SPECTRAL FLATTENING OF LASER OUTPUT IN A MULTI-LINE-LASER INSTRUMENT

(75) Inventors: Jon C. Sandberg, Erie, CO (US); Quentin A. Turchette, Boulder, CO (US)

(73) Assignee: Research Electro-Optics, Inc., Boulder, CO (US)

( * ) Notice: Subject to any disclaimer, the term of this patent is extended or adjusted under 35 U.S.C. 154(b) by 450 days.

(21) Appl. No.: 10/622,023

(22) Filed: Jul. 16, 2003

(65) Prior Publication Data

US 2004/0051869 A1    Mar. 18, 2004

Related U.S. Application Data

(60) Provisional application No. 60/396,317, filed on Jul. 16, 2002.

(51) Int. Cl.
*H01S 3/13*    (2006.01)

(52) U.S. Cl. .................. 372/31; 372/29.02

(58) Field of Classification Search ............. 372/31, 372/32, 29.01
See application file for complete search history.

(56) References Cited

U.S. PATENT DOCUMENTS

| | | | |
|---|---|---|---|
| 4,636,075 A | 1/1987 | Knollenberg | 356/336 |
| 4,798,465 A | 1/1989 | Knollenberg | 356/336 |
| 4,843,031 A * | 6/1989 | Ban et al. | 438/22 |
| 4,893,928 A | 1/1990 | Knollenberg | 356/336 |
| 4,933,541 A * | 6/1990 | Dufour | 250/202 |
| 5,085,500 A | 2/1992 | Blesener | 356/338 |
| 5,121,988 A | 6/1992 | Blesener et al. | 356/442 |
| 5,467,189 A | 11/1995 | Kreikebaum et al. | 356/336 |
| 5,491,682 A * | 2/1996 | Dohmeier et al. | 369/124.12 |
| 5,751,422 A | 5/1998 | Mitchell | 356/337 |
| 5,805,781 A | 9/1998 | McIntyre et al. | 395/117 |
| 5,872,624 A | 2/1999 | Chambers et al. | 356/73.1 |
| 6,061,132 A | 5/2000 | Girvin et al. | 356/336 |
| 6,122,043 A | 9/2000 | Barley | 356/73.1 |
| 6,185,168 B1 | 2/2001 | Kato et al. | 369/44.23 |
| 6,414,754 B1 | 7/2002 | Johnson | 356/338 |
| 6,469,831 B2 * | 10/2002 | Iizuka | 359/565 |

FOREIGN PATENT DOCUMENTS

WO    95/09354    4/1995

* cited by examiner

*Primary Examiner*—Dung (Michael) T. Nguyen
(74) *Attorney, Agent, or Firm*—Greenlee, Winner and Sullivan, P.C.

(57) ABSTRACT

An improved method of subtracting laser amplitude fluctuations from a desired signal in a multi-line laser system and a detection system having improved noise cancellation are provided. This invention reduces the noise contribution from laser amplitude fluctuations by matching the spectral dependence of the light seen at a monitor of the laser output to the spectral dependence of a desired signal. This spectral matching results in an improved correction of the laser power in a desired signal.

22 Claims, 5 Drawing Sheets

METHOD FOR NOISE CANCELLATION BY SPECTRAL FLATTENING OF LASER OUTPUT IN A MULTI-LINE-LASER INSTRUMENT

CROSS REFERENCE TO RELATED APPLICATIONS

This application claims the benefit of U.S. Provisional Application No. 60/396,317 filed Jul. 16, 2002, which is incorporated by reference to the extent not inconsistent with the disclosure herewith.

BACKGROUND OF THE INVENTION

Multi-line lasers are commonly used in a variety of instruments including those used to optically detect and size particles down to ~0.1 micron diameter. These instruments measure the light scattered from particles as they pass through the laser beam. Determination of the size of the particle is determined by the amount of scattered light that is detected. The noise floor in these instruments comes from light scattered by the background molecular gas in the particle-laser interaction region (background scattering noise) and is of two types: a fundamental noise from the photon statistics (shot noise) present even in a perfect laser and technical background scattering noise from an imperfect laser source (technical background scattering). The background scattering noise reduces the sensitivity of the instrument. Shot noise is not reducible. To improve sensitivity, methods are here described to reduce the noise from technical background scattering.

In the highest-sensitivity system, the only source of noise would be the shot noise. However, there are other sources of noise (technical background scattering) that result in lowered sensitivity and therefore, result in an increase in the size of the smallest detectable particle. One of these additional sources of noise comes from laser amplitude fluctuations. These fluctuations appear as technical background scattering on the molecular-scattered light signal above the shot noise limit. One method used to reduce the noise from laser amplitude fluctuations is to monitor the laser output to determine the fluctuations in the laser amplitude and subtract these fluctuations from the scattered light signal (or in general, any other desired signal). This type of direct subtraction, however, does not work as well as expected in a multi-line laser system. In a multi-line laser, several lasing components at different wavelengths ("lines") compete for the overall gain of the system. The relative circulating intensity of the lines can fluctuate appreciably. For example, it is possible for the overall intracavity power to remain constant (that is, the sum of the line strengths remains fixed) while the relative line strength changes. This becomes problematic when the laser output light undergoes spectral filtering, caused for example, by the use of an output optic with spectrally non-uniform transmission. If the spectral transmission of light at a monitor of laser amplitude fluctuations is different than the spectral transmission at a monitor of a desired signal, a subtraction of the laser amplitude fluctuations from the desired signal will lead to imperfect noise cancellation. This effect is not generally appreciated, yet is present in most multi-line laser systems, due to imperfect optical components.

Some methods described to reduce noise in a laser system have been described. U.S. Pat. No. 4,798,465 (Knollenberg, Jan. 17, 1989) and continuation-in-part U.S. Pat. No. 4,893,928 (Knollenberg, Jan. 16, 1990) describe a particle detection device having background noise reduction. The noise reduction is achieved by use of a plurality of linear detectors, where each detector senses a portion of the optical path. The signals from the detectors are parallel processed to reduce the effect of background molecular scattering. U.S. Pat. No. 6,061,132 (Girvin, May 9, 2000) describes a particle counter having a dual detector array, wherein a detector in one array is used for noise cancellation, a detector in the other array is used to detect the signal from a particle, and the signals are subtracted to reduce the noise. U.S. Pat. No. 5,467,189 (Kreikebaum, Nov. 14, 1995) describes a particle sensor which subtracts background scattering signals from particle signals. U.S. Pat. No. 5,121,988 (Biesener, Jun. 16, 1992) describes a particle detector having monitoring of laser output power and adjustment of the current supplied to the laser to compensate. U.S. Pat. No. 6,414,754 (Johnson, Jul. 2, 2002) describes use of an ionic coloring agent on portions of the instrument to absorb stray light.

None of the above methods describes a method to cancel the laser amplitude noise fluctuation component in a multi-line laser system. An improved method of canceling the laser amplitude noise fluctuation component from a desired signal in a multi-line laser system is needed.

SUMMARY OF THE INVENTION

The invention provides an improved method of subtracting the laser amplitude fluctuations from a desired signal in a multi-line laser system, and a detection system having improved noise cancellation. This invention reduces the noise contribution from laser amplitude fluctuations by matching the spectral dependence of the light seen at a monitor of the laser output (output monitor detector) to the spectral dependence of the desired signal. There are many methods to accomplish this, as described herein. In one embodiment of the invention, an output coupler that has a spectrally flat transmission of the laser lines is used to pass light from the laser cavity into an output monitor detector which monitors laser amplitude fluctuations, instead of an output coupler that has an unequal transmission of the laser lines, as normally found in standard couplers. Using a spectrally flat output coupler in the optical path of an output monitor detector will result in improved noise cancellation and improve the sensitivity of the instrument when the laser amplitude fluctuations are subtracted from the desired signal.

In a specific embodiment, light from a multi-line laser is monitored in two paths, a laser output monitor path (monitored using an output monitor detector) and a desired signal path (monitored using a signal detector). Light from the laser output is passed through one or more spectral matching optics into the output monitor detector. The gain of the output monitor detector is adjusted so that the laser amplitude fluctuations in the desired signal path and the laser output monitor path are equal, forming a corrected signal. This corrected signal is subtracted from the desired signal, for example a scattered light signal.

"Spectral matching optics" are one or more optics used in the optical path of the desired signal or the laser output monitor path to make the spectral content of the desired signal and the laser output more equal than if the spectral matching optics are not used. "Spectral matching optics" do not necessarily make the spectral content of the desired signal and the laser output equal. As used herein, a "spectrally flat optic" indicates that the transmission of any two or more different wavelengths through the spectrally flat optic is more closely equal than in the standard optic. This criteria will depend on the wavelength range of interest, but for example, a standard optic may have 100% variation across the range of interest, while a spectrally flat optic may have 20%. Ideally, the transmission of the different wavelengths passing through a spectrally flat optic is exactly the same, but due to various factors, the transmission may not be exactly the same. The use of a "spectrally flat" optic in the methods described herein gives a detected signal that has lower noise than the use of another type of optic (for example, a standard optic). As long as the optic has the desired effect of reducing noise in a detected signal, the optic is considered "spectrally flat". One or more optics can be combined to produce a spectrally flat optic. As used herein, "canceling" or "reducing" means removal of some or all of the noise present in the desired signal.

DETAILED DESCRIPTION OF THE INVENTION

The invention may be further understood by reference to the following description and the Figures, where like numbers indicate like features. Although the desired signal is exemplified by a scattered light signal, it is to be understood that scattered light is not the only possible desired signal, and the invention can be applied to other desired signals.

When the desired signal is a scattered light signal, the analysis presented herein is a simplification which ignores an inherent spectral sensitivity present in the scattering signal that is not present in the output signal. The strength of the molecular-scattered signal obeys the "Rayleigh dependence", that is, the strength of the scattered signal is inversely proportional to the fourth power of the wavelength. Thus laser lines that are shorter in wavelength than other lines will scatter more strongly. In standard systems, imperfections in the optics will dominate this Rayleigh dependence, but if measures are taken to reduce the effect of optic imperfections as described herein by spectral matching then the Rayleigh scattering dependence must be and can be taken into account for optimum noise cancellation, either by appropriate spectral shaping of the output coupler or by using a compensating optic ("Rayleigh optic") and the methods described herein and known in the art without undue experimentation.

Laser amplitude fluctuations are normally monitored by passing some portion of the light from the laser through an output coupler to an output monitor detector. The signal at the output monitor detector is subtracted from a desired signal, for example a scattered light signal. However, if the laser light has contributions from multiple wavelengths, any change in the relative intensity of the wavelengths creates an imperfect subtraction if the signal at the output monitor detector and the desired signal do not have the same spectral dependence.

In one embodiment, the invention comprises a multi-line laser, a spectrally flat output coupler to pass a portion of light from the laser to a detector (output monitor detector) and a detector to measure a desired signal (signal detector). The signal from the output monitor detector is passed through an electronic gain stage and subtracted from the signal from the signal detector. The gain is adjusted to minimize the noise in the desired signal. Once a spectrally flat optic is in place, the subtraction will not depend on the details of the spectral content of the laser, which in general are not measured and are time-varying. The signal detector can detect any desired signal that is initiated using the laser that includes a noise contribution from laser amplitude fluctuations.

In the case when the desired signal is scattered light, the total scattered signal at the signal detector is (not accounting for the Rayleigh scattering dependence)

$$S_{scat} = I_1 + I_2 + I_3 + \ldots + I_n + \ldots + I_N + S_{signal},$$

where the $I_n$ are the circulating intensities of the various laser lines at corresponding wavelengths $\lambda_n$. There are N such lines. The desired signal is denoted $S_{signal}$, which implicitly contains the non-reducible shot-noise. The circulating light is partially transmitted through the output coupler and gives rise to an output monitor signal:

$$S_{mon} = G(I_1 T(\lambda_1) + I_2 T(\lambda_2) + \ldots + I_n T(\lambda_n) + \ldots + I_N T(\lambda_N))$$

where G is an overall gain applied to the output monitor signal, and $T(\lambda_n)$ is the transmission of the output coupler at wavelength $\lambda_n$. Note that the output monitor signal does not contain $S_{signal}$. The difference signal used in noise cancellation is $$S_{scat} - S_{mon} = I_1[1 - GT(\lambda_1)] + \ldots + I_N[1 - GT(\lambda_N)] + S_{signal}$$

Noise cancellation will be compromised if T is not flat. In other words, perfect cancellation occurs only when $$T(\lambda_1) = T(\lambda_2) = \ldots = T(\lambda_n) = \ldots = T(\lambda_N)$$

(and G is set properly). Furthermore, the cancellation when this condition is met does not depend on the (time-variable) $I_n$, in other words, the cancellation does not depend on the spectral content of the laser. The slightly more complicated mathematics including the Rayleigh dependence is not included here, but can be accounted for by a transmission function T which compensates for the $1/\lambda^4$ dependence of scattering strength, as known in the art.

Figure 1:
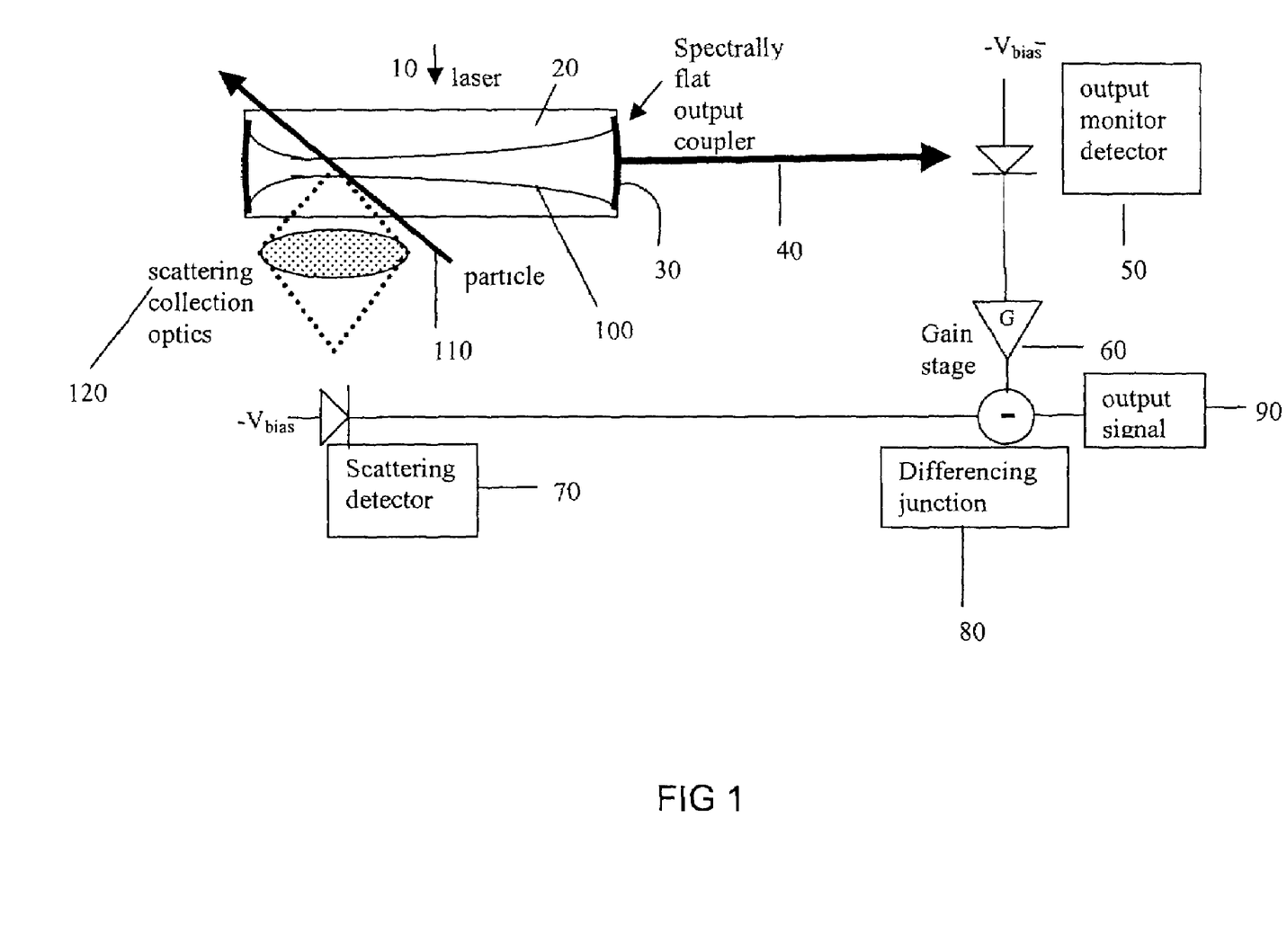
FIG. 1 shows a schematic illustration of one of the embodiments of the invention.

FIG. 1 shows one embodiment of the invention. Laser 10 has cavity 20. One optic of cavity 20 is spectrally flat output coupler 30. Light from cavity 20 passes through spectrally flat output coupler 30 in path 40 which is optically connected to and detected by output monitor detector 50 (in one embodiment, a photodiode). Output monitor detector 50 is electrically connected to gain stage 60.

In FIG. 1, the desired signal is the signal from light scattered as particles pass through the laser beam 100 through path 110. The scattered light from the particles is collected by collection optics 120 and is detected by scattering detector 70. Signal from gain stage 60 is subtracted from the signal from scattering detector 70 at differencing junction 80 to form output signal 90. Particle events are present only on the scattering detector and not on the output monitor. The net result is improved signal-to-noise when particles are present in the laser path. Although not shown in the Figures, all associated electronics and optical elements required are included as known in the art.

To correct for the Rayleigh dependence of scattered light, where the scattering strength is proportional to the inverse of wavelength to the fourth power, a compensating optic ("Rayleigh optic") that has the same dependence on wavelength may be placed in any convenient location in the system, for example, as the output coupler or a compensating optic, so that both the scattered signal and output monitor signal have the same dependence on wavelength. Alternatively, the scattering signal can be passed through a compensating optic ("Rayleigh optic") to correct for the Rayleigh dependence.

The detectors or detecting elements may be one or more detectors such as photodiodes, photomultiplier tubes, or any optical-to-electrical sensor, as known in the art. As used herein, "detector" includes the actual detector, plus associated electronics, plus associated optical elements, as known in the art. Appropriate detectors, gain stages and other electrical components are known in the art.

In one embodiment, the laser is a Helium-Neon (He—Ne) type gas laser with nominal wavelength of 632.8 nm. This laser also has several strong laser lines ranging in wavelength from 600 nm to 650 nm. Because of such nearby lines, it is difficult to manufacture high-circulating-power single-line lasers (single-line lasers would not suffer from fluctuating relative line strength). A typical HeNe laser output coupler has a variation in transmission from 600 nm to 650 nm of a factor of two or more. A spectrally flat optic may be prepared using standard techniques known in the art, for example ion beam sputtering. Suitable spectrally flat optics are made by Research Electro-Optics, Inc., Boulder, Colo. and can be fabricated by other optics suppliers. Optics that have spectral variation of 20% over the observed laser lines have been used in the methods and devices of this invention, giving superior noise cancellation than obtained if an optic with a non-spectrally flat output is used. Optics with other amounts of spectral variation may be used, as described herein and known in the art, as long as they reduce the noise present in the desired signal.

Figure 2:
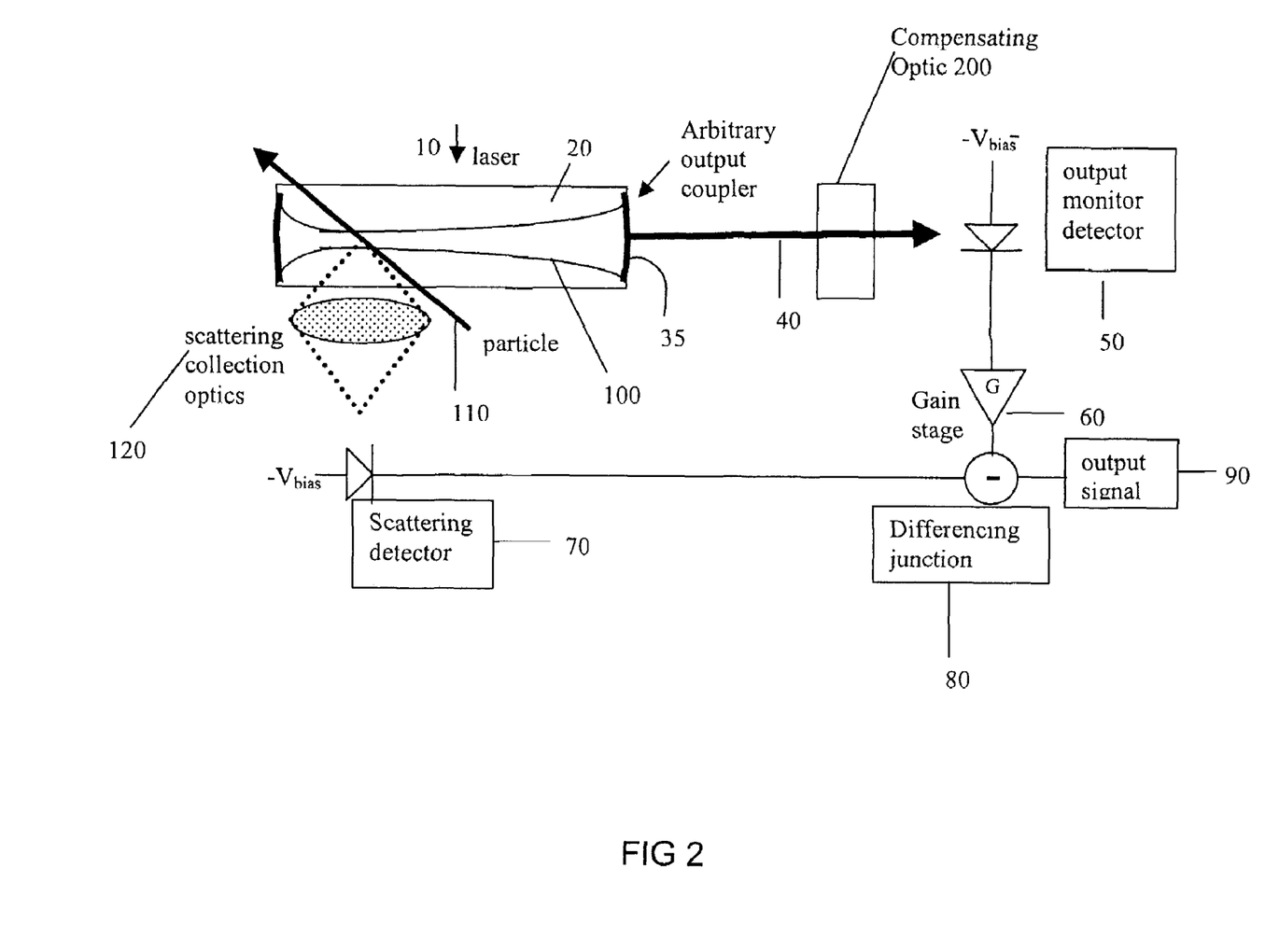
FIG. 2 shows a schematic illustration of a second embodiment of the invention using an output coupler with an arbitrary spectral transmission, along with a compensating optic.

The use of any means to match the spectral output of a laser monitor signal and a detected signal is included in this invention. Another method for carrying out the invention is shown in FIG. 2 and includes using a standard (or arbitrary) partially reflective mirror 35 as normally found in a variety of multi-line lasers to pass a portion of the laser output into a detector to monitor the laser output. The output from the standard optic is then passed into another optic (compensating optic 200) which flattens the spectral output. The other components of the system and operation of the system is as shown and described for FIG. 1. Other configurations of the invention are included including using one or more matching optics in any optical path, so that the spectral dependence of a monitor of the desired signal matches the spectral dependence of a monitor of laser amplitude fluctuations. The matching optics can be present in either the monitor path or the desired signal path, or both.

Figure 3:
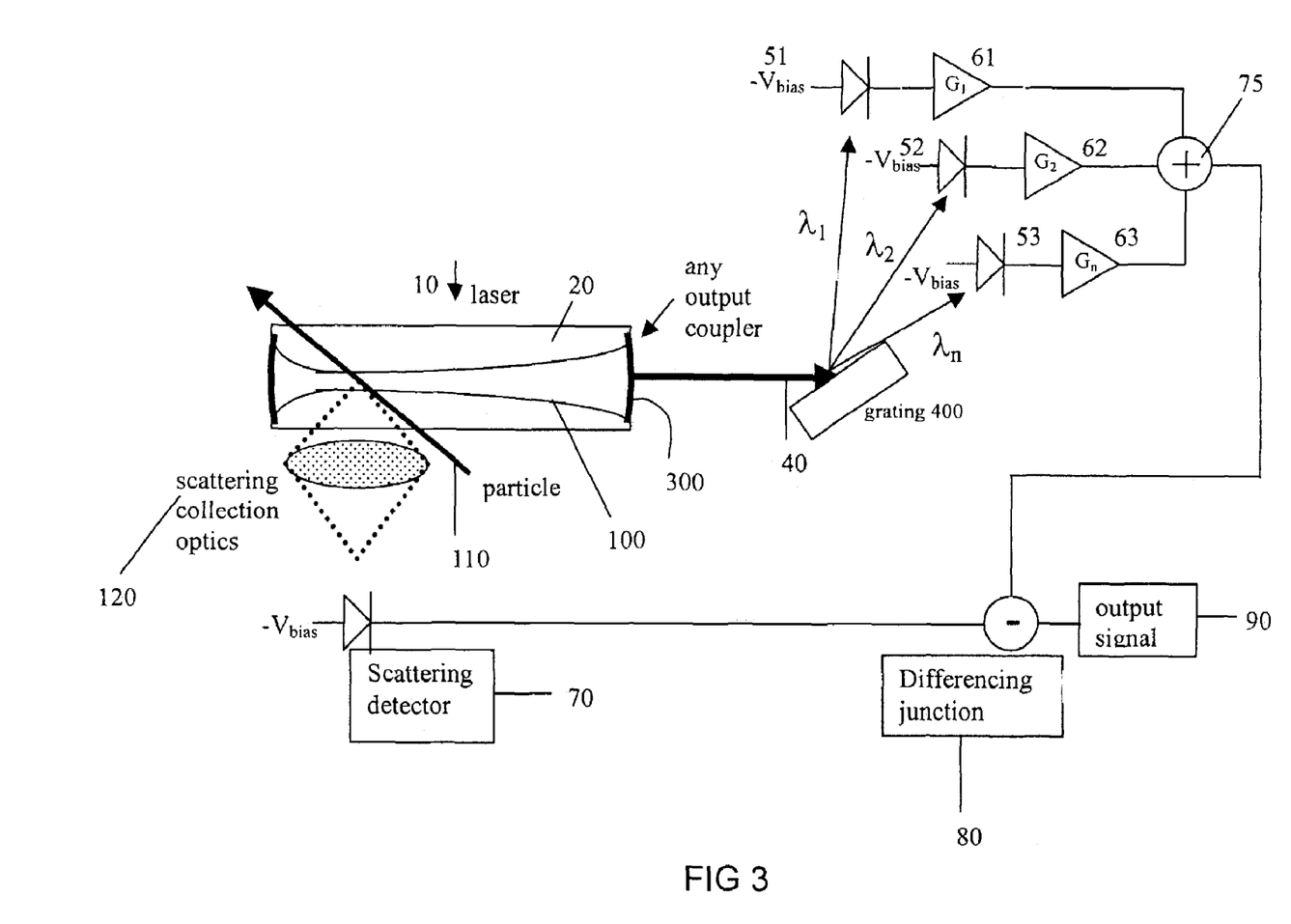
FIG. 3 shows an embodiment in which the laser output is spatially-divided into its constituent wavelength components using a grating. Each wavelength component strikes a unique detector and is amplified by its own gain stage. In this embodiment, the output coupler is arbitrary and there is no need for a compensating optic.

As specifically exemplified herein, a spectrally flat optic or a compensating optic is used to match the spectral response in the monitor and signal paths. However, these are not the only ways to achieve the desired noise cancellation. For example, the spectral components of the laser (lines) can be separated (using a grating or other spectral separating device, as known in the art) and each line can be individually adjusted for the desired noise cancellation. Each line can illuminate its own detector, and the gain of each detector adjusted. The outputs of all detector gains are summed and the sum is subtracted from the desired signal. FIG. 3 shows an embodiment of the invention where light from laser 10 is passed from cavity 20 through any output coupler 300 in path 40. Light path 40 is optically connected with grating 400, where the wavelengths of laser 10 are spatially separated. In FIG. 3, three wavelengths are shown ($\lambda_1$, $\lambda_2$ and $\lambda_n$), although it is understood that all lines are separated as long as the grating has sufficient resolution. Each line is in optical communication with a detector (51, 52 and 53 in FIG. 3) and gain stage (61, 62 and 63 in FIG. 3). The outputs of the gain stages are summed at summing point 75 and the sum is subtracted from the desired signal at differencing junction 80. Separate detectors and gain stages are shown in FIG. 3, but this is not the only possible configuration. For example, a movable detector can be used, wherein each line passes sequentially into the detector and the gain is adjusted, and stored electronically for summing and subtraction, as described above. The other components and operation of the device illustrated in FIG. 3 is the same as described elsewhere herein.

For optimal noise cancellation, the spectral response of the optics in the signal and monitor paths must be considered. Usually, the same materials are used in the optical paths and the spectral response effect will cancel. However, if different materials are used in the optics, compensation through the use of appropriate optics must be made, for optimal noise cancellation. For example, if the detectors in the optical paths are made from different materials, a compensating optic must be used in one or both paths to counteract this effect. The use of compensating optics to correct for differences in spectral response is known by one of ordinary skill in the art without undue experimentation.

Figure 4:
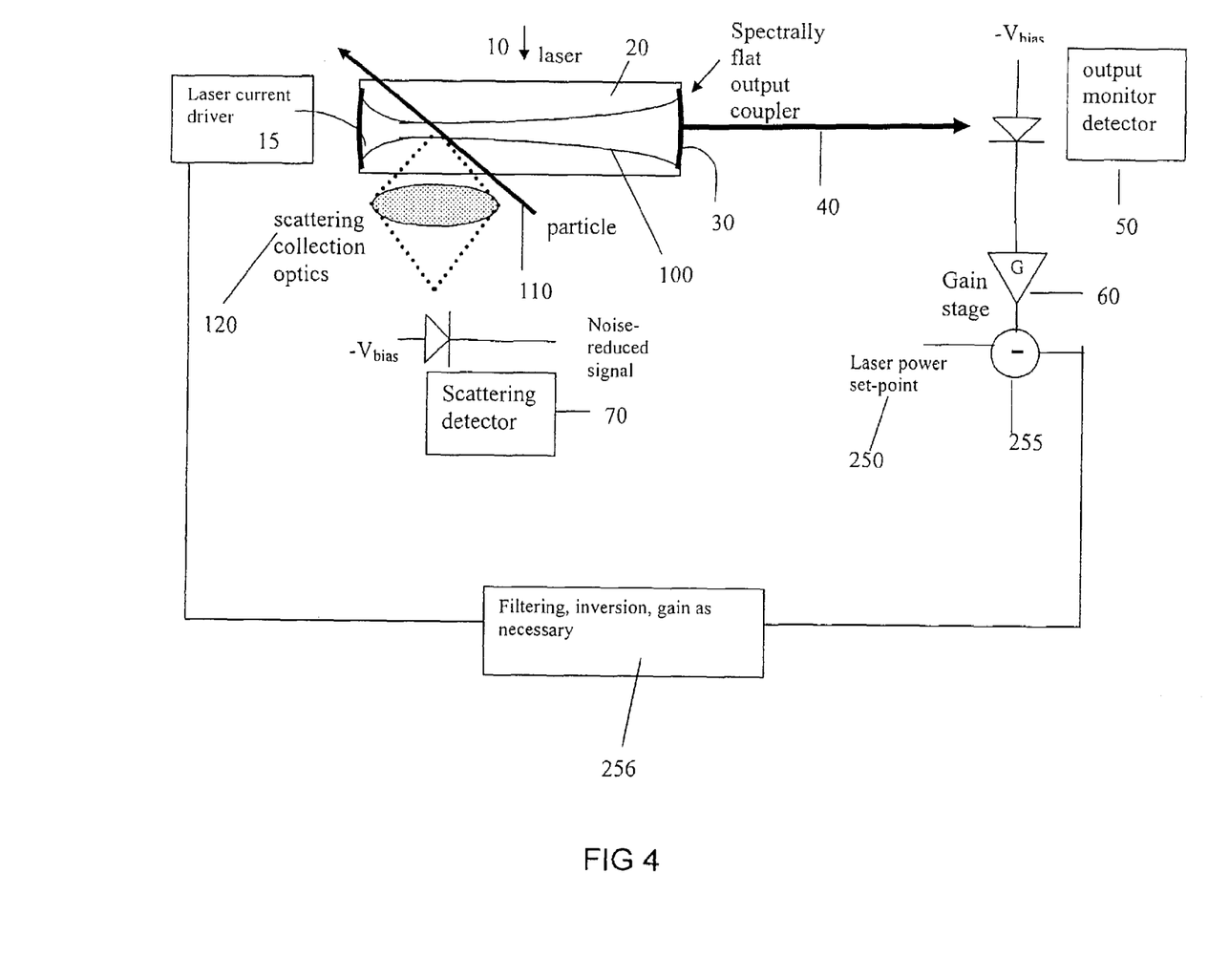
FIG. 4 shows one embodiment using active noise cancellation.

The methods described herein can be used in an active method of noise cancellation. In active noise cancellation, the power at the output monitor detector is monitored and information is fed back to some element of the laser that controls its power. When the power in the laser is lower than a selected laser power setpoint, the laser current is increased to compensate for this and when the power rises higher than a selected laser power setpoint, the laser current is dropped. This is a standard closed-loop feedback laser noise control system. In a multi-line laser, the normal practice will not produce optimum results if the desired noise-reduced signal derives directly from the intracavity intensity, since the output monitor detector and the scattering detector have different spectral dependence, as described above. In active noise cancellation with correction for spectral dependence shown for example in FIG. 4, the techniques described above are used to correct for the spectral dependence of the optics involved. The signal after correction (after gain stage 60) is compared to a desired laser power set-point 250 at comparing junction 255. As required, a parameter of the laser (current is shown in FIG. 4) is adjusted to compensate for increases or decreases in laser power. In FIG. 4, laser current driver 15 is electrically connected to both laser 10 and comparing junction 255. If required or desired, the feedback signal after comparing junction 255 is electrically connected with adjustment mode 256, where filtering, inverting or gain adjustment is performed, as necessary or desired. Adjustment mode 256 is electrically connected with laser current driver 15. Active stabilization of laser intensity is generally known, but known methods of stabilization do not take into account spectral content corrections of the laser output signal. Using the teachings herein, active stabilization of intracavity laser intensity can contain correction for spectral dependence differences of the output monitor detector and scattering detector. Shown in FIG. 4 is a spectrally flat output coupler, however, any output coupler and compensating optic configuration may be used, as described herein.

Figure 5:
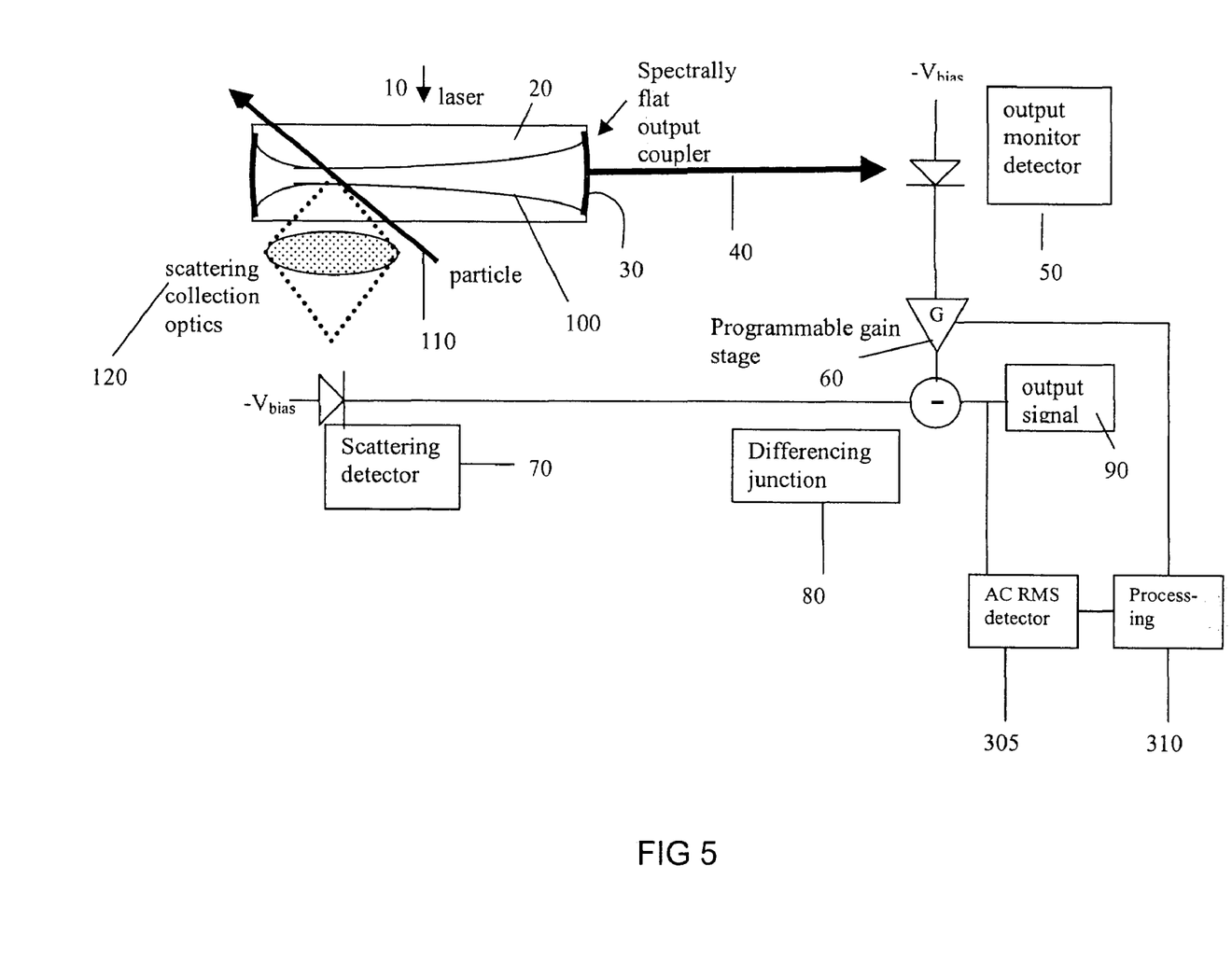
FIG. 5 shows one embodiment using automatic noise cancellation.

In another embodiment of the invention, the noise cancellation in a multi-line laser system can be automated. In its most general form, the desired signal is measured and a level of the noise is established. Using the noise level, one of a number of parameters in the system can be adjusted to minimize the noise automatically, with no intervention from a user. For example, it is straightforward to measure the root-mean-square (RMS) noise in an electronic signal. The RMS noise can be measured, processed and fed into a programmable gain stage to automatically adjust the level of a compensating signal to minimize the RMS noise. One example of automated noise cancellation is shown in FIG. 5. In FIG. 5, the RMS noise is detected by detector 305. The RMS noise is measured, processed using processing 310 and a parameter of the system, for example gain at gain stage 60 is automatically adjusted to reduce the RMS noise. As one example, a microprocessor can be employed to try a series of parameter-adjustment and noise-measurement cycles until an optimum level of noise is achieved. Other parameters of the system are as described herein. Other elements which can be adjusted automatically by the processor include, but are not limited to electrical gain and filtering stages (analog or digital), and electronically controlled optical attenuators. Automatic noise reduction has the benefit of eliminating any manual adjustment of signals in the set-up stage of an instrument, but also maintains optimal noise-cancellation when parameters are changing in the system due to change in environment. For example, the strength of the molecular background scattering signal depends on the atmospheric pressure in which the instrument is operated. As the ambient air density gets lower, the scattered signal size gets lower and therefore a gain in the system requires adjustment in order to maintain optimal noise cancellation. This can be done by measuring the noise directly to adjust the gain automatically or by measuring the atmospheric pressure and using this to adjust the gain. Ambient gas composition also affects the molecular-scattered signal size.

An additional factor that should be considered for maximum noise cancellation is the effect that different bandwidths of the electronics have on the signal. If the amplitude and phase of electronics in the signal path and output monitor path do not match, a different contribution from the electronics to the signal will create an imperfect cancellation. For maximum noise cancellation, the bandwidths of all electronic paths should be matched. This bandwidth or phase matching can be performed using a number of methods known in the art, including filters such as resistor-capacitor lowpass, bandpass, high-pass, lead-lag filters or others. Alternatively, the entire process could be performed in the digital domain using analog-to-digital converters and digital signal processing techniques as known in the art.

Although all adjustments to the signal are shown in the output monitoring arm of the optical setup in the Figures shown and discussed herein, it is to be understood that this is not the only possible configuration. Those of ordinary skill in the art will recognize that the adjustments may be made in the scattering arm, or a combination of the two arms of the instrument. For example, some of the spectral matching optics could be incorporated in the scattering collection optics and some of the electronic gains and post-processing could be connected to the scattering detector. These embodiments are known to one of ordinary skill in the art with the description provided herein.

Although the description above contains many specificities, these should not be construed as limiting the scope of the invention, but as merely providing illustrations of some of the preferred embodiments of the invention. For example, any laser that contains more than one wavelength may be used. The noise reduction method described herein may be used by itself, or combined with other noise reduction methods, as known in the art. Also, optics may be used other than those specifically described herein. All references cited herein are hereby incorporated by reference to the extent not inconsistent with the disclosure herein.

We claim:

1. A method for reducing noise from laser amplitude fluctuations in a desired signal generated by a multi-line laser comprising:
   detecting the desired signal;
   monitoring the amplitude fluctuations of the multi-line laser source;
   matching the spectral dependence of a monitor of amplitude fluctuations of the multi-line laser source to the spectral dependence of the desired signal, forming a matched monitor signal;
   subtracting the matched monitor signal from the desired signal.

2. The method of claim 1, further comprising applying a Rayleigh correction to the multi-line laser output or the desired signal.

3. The method of claim 2, wherein applying the Rayleigh correction comprises passing one or both of the desired signal or output of the multi-line laser through a Rayleigh optic.

4. The method of claim 1, wherein the desired signal is a scattered light signal.

5. A method for reducing noise from laser amplitude fluctuations in a desired signal generated by a multi-line laser comprising:
   passing a portion of the output of the multi-line laser through a spectrally flat optic, forming a laser monitor signal;
   monitoring the desired signal;
   adjusting the intensity of the laser monitor signal so that laser amplitude fluctuations in the desired signal and the laser monitor signal are equal, forming a corrected signal;
   subtracting the corrected signal from the desired signal.

6. The method of claim 5, wherein the desired signal is a scattered light signal.

7. The method of claim 5, further comprising applying a Rayleigh correction to the multi-line laser output or the desired signal.

8. The method of claim 7, wherein applying the Rayleigh correction comprises passing either the multi-line laser output or the desired signal through a Rayleigh optic.

9. A method for reducing noise from laser amplitude fluctuations in a desired signal generated by a multi-line laser, comprising:
   passing a portion of the output of the multi-line laser through an output coupler, forming a laser output signal;
   passing the laser output signal through a compensating optic, forming a laser monitor signal, wherein the spectral dependence of the laser monitor signal matches that of the desired signal;

subtracting the laser monitor signal from the desired signal.

10. The method of claim 9, further comprising applying a Rayleigh correction to the output of the multi-line laser or the desired signal.

11. The method of claim 10, wherein applying the Rayleigh correction comprises passing either the output of the multi-line laser or the desired signal through a Rayleigh optic.

12. The method of claim 9, further comprising
adjusting the intensity of the laser monitor signal so that laser amplitude fluctuations in the desired signal and the laser monitor signal are equal, forming a corrected signal;
subtracting the corrected signal from the desired signal.

13. The method of claim 9, wherein the desired signal is a scattered light signal.

14. A laser scattering system having reduced noise comprising:
a laser cavity having output along a laser beam axis;
an output coupler coupled to one end of the laser cavity along the laser beam axis;
a compensating optic in optical communication with the output coupler;
an output detector in optical communication with the compensating optic;
a gain adjusting element in electrical communication with the output detector;
a scattered light detector at a selected angle away from the laser beam axis;
a differencing junction in electrical communication with the gain adjusting element and in electrical communication with the scattered light detector.

15. The system of claim 14, wherein the output coupler is spectrally flat.

16. The system of claim 14, further comprising one or more Rayleigh optics.

17. A method of actively reducing laser amplitude fluctuation noise from a desired signal comprising:
passing a portion of the output of a multi-line laser through a spectrally flat output coupler, forming a laser monitor signal;
comparing a desired laser output setpoint to the intensity of the laser monitor signal;
adjusting the laser output so that the intensity of the laser monitor signal is the same as the desired laser output setpoint;
whereby the laser amplitude fluctuation noise in the desired signal is reduced.

18. The method of claim 17, wherein the desired signal is a scattered light signal.

19. A method of automated laser amplitude noise reduction from a desired signal comprising:
passing a portion of the output of a multi-line laser through a spectrally flat output coupler, forming a laser monitor signal;
monitoring the scattered light signal;
adjusting the intensity of the laser monitor signal so that fluctuations in the desired signal and the laser monitor signal are equal, forming a corrected signal;
subtracting the corrected signal from the desired signal.

20. The method of claim 19, wherein the desired signal is a scattered light signal.

21. The method of claim 1, further comprising adjusting the intensity of the matched monitor signal so that the laser amplitude fluctuations in the desired signal and the matched monitor signal are equal.

22. The method of claim 1, wherein the desired signal is monitored at a selected angle away from the axis of the multi-line laser.

* * * * *